United States Patent [19]

Sioshansi et al.

[11] Patent Number: 4,743,308

[45] Date of Patent: May 10, 1988

[54] CORROSION INHIBITION OF METAL ALLOYS

[75] Inventors: Piran Sioshansi, Bedford; Ward D. Halverson, Cambridge, both of Mass.

[73] Assignee: Spire Corporation, Bedford, Mass.

[21] Appl. No.: 4,599

[22] Filed: Jan. 20, 1987

[51] Int. Cl.⁴ .............................................. C23C 14/00
[52] U.S. Cl. ....................................... 148/4; 148/900; 204/192.31
[58] Field of Search ...................... 148/4, 900, 425.13; 428/687; 427/42; 204/192 N

[56] References Cited

U.S. PATENT DOCUMENTS

| | | | |
|---|---|---|---|
| 3,900,636 | 8/1975 | Curry et al. | 148/4 |
| 3,925,116 | 12/1975 | Engel | 148/4 |
| 4,465,524 | 8/1984 | Dearnaley et al. | 148/4 |

OTHER PUBLICATIONS

Sioshansi et al., "Wear Improvement of Surgical Titanium Alloys by Ion Implantation;" *J. Vac. Sci. Tech.* A3(6), Nov./Dec. 1985; pp. 2670 et seq.

J. M. Williams et al., "Ion Implantation of Surgical Ti-6Al-4V Alloy;" *International Conference on Surgical Modification,* Heidelberg, Sep. 17-21, 1984.

L. Block et al., "Serum Concentration of Chromium, Cobalt & Nickel after Total Hip Replacement: a 6 mos. study; *"Biomaterials,* 12/1983, vol. 4, p. 160.

A. Koezel et al., "Release of Corrosive Products by F-75 Cobalt Base Alloy in the Rat. I: Acute Serum Elevations: *J. Biomed. Mat. Res.* vol. 18, 513-522 (12/1984).

J. L. Woodsman et al., "Isolation of Serum Protein Organometallic Corrosive Products from 316LSSS & HS-21 in vitro & in vivo; "*J. Bio. M. R.* vol. 18, 99-114, 12(1984).

W. C. Oliver et al., "The Wear Behavior of Nitrogen-Implanted Metals;" Metallurgical Transactions; ISA, Dec. 1984, 2221-2229.

*Primary Examiner*—L. Dewayne Rutledge
*Assistant Examiner*—S. Kastler
*Attorney, Agent, or Firm*—Morse, Altman, Dacey & Benson

[57] ABSTRACT

A metal alloy with a treated surface and the process of effecting the treated surface are disclosed whereby its ion release under static, stress and crevice corrosion and corrosive wear conditions is reduced. The metal alloy preferably is an ASTM F-75 Co-Cr-Mo alloy. The preferred process includes providing a workpiece formed of such a metal alloy with a coating of biologically compatible elements, such as a noble metal and then exposing the thus coated surface thereof to bombardment by an ion beam, whereby a plurality of noble metal atoms, together with a plurality of ions from the beam, are driven into the surface of the workpiece a certain distance. Another preferred process includes the direct ion implantation of a workpiece with biocompatible elements, such as nitrogen, tantalum and inert gas ions. Preferably, such a workpiece finds application as an orthopaedic implant.

3 Claims, 3 Drawing Sheets

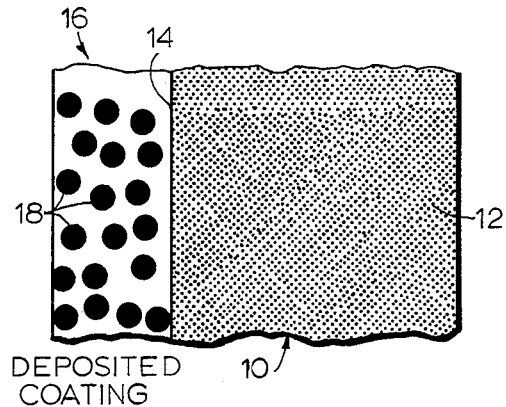
FIG. 1
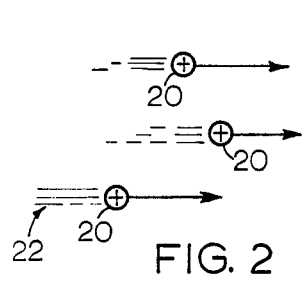
FIG. 2
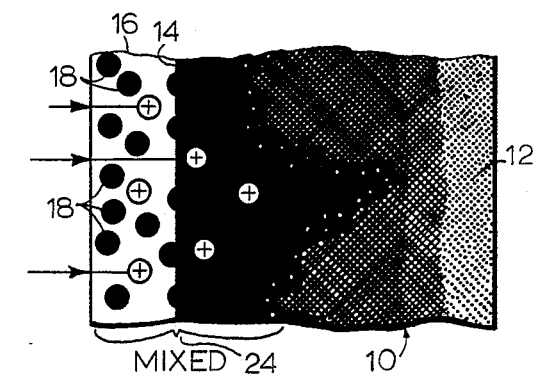
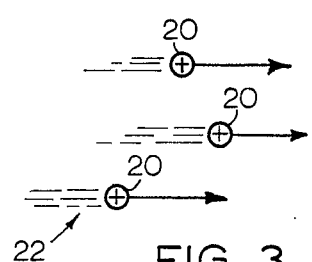
FIG. 3
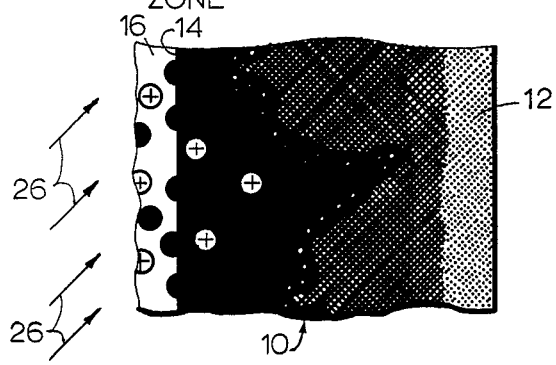
FIG. 4
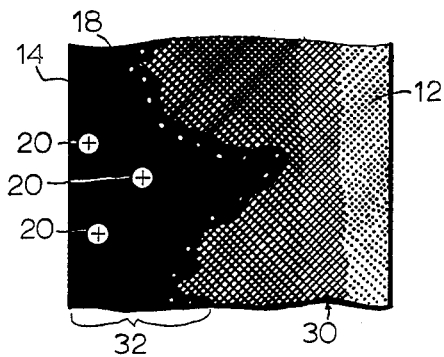

CORROSION INHIBITION OF METAL ALLOYS

BACKGROUND OF THE INVENTION

1. Field of the Invention

The present invention relates generally to corrosion inhibition of metal alloys and, more particularly, to corrosion inhibition of a Co-Cr-Mo alloy (ASTM F-75) and the process of effecting the same.

2. The Prior Art

In the specialized field of orthopaedic prostheses used for human joint replacement and fixation devices, cobalt-based alloys have become widely used. The specific cobalt-based alloy designated for this purpose by the American Society for Testing and Materials (ASTM) is known as the F-75 Co-Cr-Mo alloy, also called "Vitallium" or "HS-21" alloy. There is presently considerable concern that metallic ions, principally chromium, cobalt and nickel, released by corrosion of the cobalt-based metal alloy after implantation of the prosthesis, can cause adverse long term local and systemic effects in the recipients of the implanted orthopaedic devices. Patients receiving such Co-Cr-Mo alloy joint replacements have been observed with elevated levels of cobalt in their blood, urine, hair, muscle and bone adjacent the implant as well as in remote internal organs.

SUMMARY OF THE INVENTION

It is a principal object of the present invention to overcome the above disadvantages by providing a Co-Cr-Mo alloy for use as an orthopaedic surgical implant with a surface that is treated whereby its ion release under static, stress and crevice corrosion and corrosive wear conditions is materially reduced and, the process of effecting such surface treatment.

More specifically, it is an object of the present invention to provide a Co-Cr-Mo alloy used as an orthopaedic surgical implant with a modified passive surface layer such that its electrochemical corrosion voltage comes within a range in which self-passivation of its surface occurs spontaneously even after removal of all or portions of the passive layer by mechanical, electrical or chemical means. This modified passive surface layer of the Co-Cr-Mo alloy includes atoms of biologically compatible elements, such as a noble metal, and ions of an inert gas intermixed with atoms of the Co-Cr-Mo alloy to a depth ranging from about 0.2 to about 200 nanometers. Preferably, the biocompatible element is one of a group including platinum, gold, palladium, tantalum, nitrogen and the like. Preferably, the inert gas is one of a group including ionized argon, neon, helium, krypton, and the like. The process of passivating the electrochemically active surface of the Co-Cr-Mo metal alloy includes the formation of a coating of the noble metal on the surface of the Co-Cr-Mo metal alloy, followed by exposing the thus coated surface to an ion beam, whereby a plurality of noble metal atoms together with a plurality of ions are driven into the Co-Cr-Mo metal alloy surface to a depth of at least about 0.2 nanometers, forming thereby a mixed zone at and immediately below the Co-Cr-Mo metal alloy surface in which the noble metal atoms and the ions are thoroughly intermixed with the atoms of the Co-Cr-Mo metal alloy. The result is an orthopaedic surgical implant formed of such Co-Cr-Mo metal alloy having a treated surface whereby its corrosion resistance is considerably improved such that its ionization in the environment of the human body is materially reduced.

Other objects of the present invention will in part be obvious and will in part appear hereinafter.

The invention accordingly comprises the surface-treated Co-Cr-Mo metal alloy and the process of effecting such surface treatment of the present disclosure, its steps, components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 1 is a schematic side elevation, on an enlarged scale, of a fragmentary portion of a Co-Cr-Mo metal alloy having a coating of a biocompatible element formed thereon;

FIG. 2 is a view similar to that shown in FIG. 1, but illustrates the exposing of the coated Co-Cr-Mo metal alloy to an ion beam;

FIG. 3 is a view similar to that shown in FIG. 2, but illustrates the removal of the coating from the Co-Cr-Mo metal alloy surface while the same is exposed to the ion beam;

FIG. 4 is a view similar to that shown in FIG. 3, but illustrates the Co-Cr-Mo metal alloy after the completion of the removal of the coating from its surface;

DETAILED DESCRIPTION OF THE PREFERRED EMBODIMENT

Figure 5:
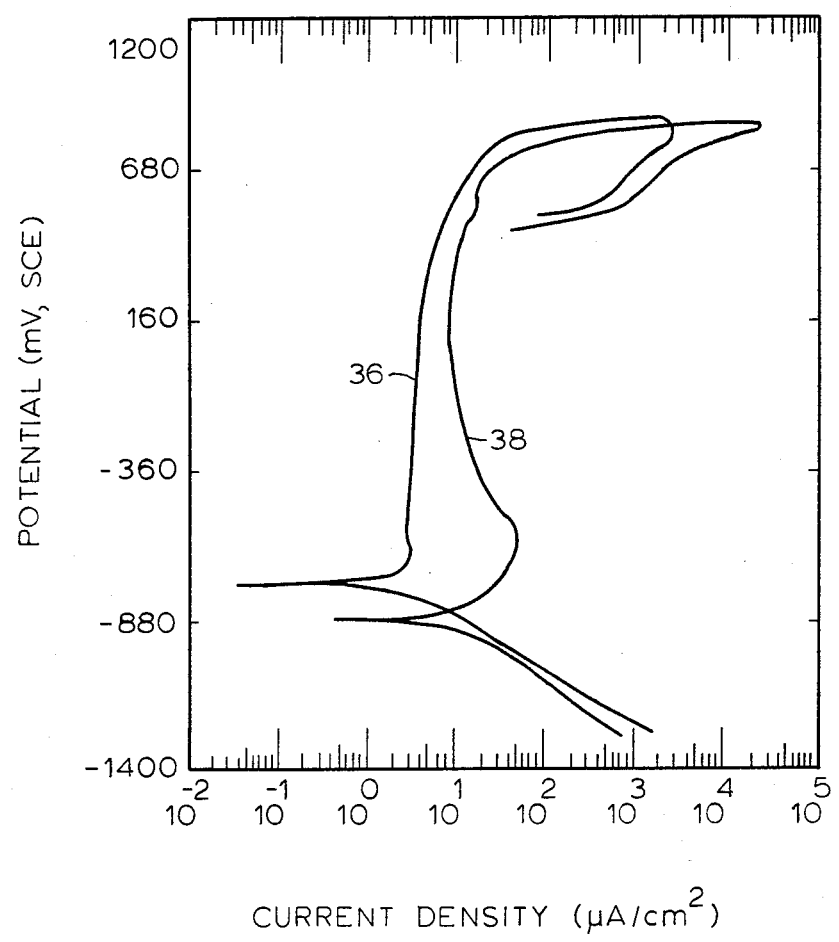
FIG. 5 illustrates the electrochemical response of a Co-Cr-Mo metal alloy which has been treated according to the invention versus a Co-Cr-Mo metal alloy which has not been so treated.

In general, the present invention relates to a metal alloy whose surface has been treated so that its ion release under static, stress and crevice corrosion and corrosive wear conditions is materially reduced and, to a process of effecting such surface treatment.

The metal alloy preferably is a Co-Cr-Mo alloy, useful primarily as an alloy for making orthopaedic surgical implants. Such orthopaedic surgical implants are used for human joint replacements and fixation devices, including artificial knees, hips, or other articulating joints, such as shoulders, elbows and the like. The specific cobalt-based alloy approved for orthopaedic surgical implants in humans by the American Society for Testing and Materials (ASTM) is designated as the F-75 Co-Cr-Mo alloy, also known as "Vitallium" or "HS-21" alloy. One preferred specification of an ASTM F-75 alloy is: Cr 27–30%, Ni 2.5% max., Fe 0.75% max., C 0.35% max., Mo 5–7%, with the balance of about 63% being cobalt (Co). Another preferred specification of an ASTM F-75 alloy is: Cr 27–30%, Ni 2.5 max., Fe 0.75% max., C 0.35% max., in lieu of molybdenum however, Mn 1% max., and Si 1% max., with the balance of about 65% again being cobalt (Co).

Cobalt-based alloys, when used as artificial implants, exhibit a potential severe and harmful drawback: they release corrosion products into the human body. Recently, the release of corrosion products by implants has become a matter of concern. So much so that some surgeons have abandoned cobalt-based alloys altogether in favor of titanium-based alloys, which evince, among others, high corrosion resistance. The use of titanium-based alloys for orthopaedic surgical implants has been beset by other problems, however. See, for example, a co-pending application entitled "Ion Implantation of Titanium Workpieces without Surface Discoloration," Ser. No. 861,845, filed May 12, 1986 and assigned to a common assignee. (A process involving the ion implantation of plastics in order to enhance their surface hardness is disclosed in another co-pending application Ser. No. 915,414, filed Oct. 6, 1986, and also assigned to the common assignee herein.)

The release of the elements chromium, cobalt and nickel by cobalt-based implants has created most of the concern. Following such implants, elevated levels of cobalt and nickel have been observed in the kidneys, spleen and lungs of the recipients, while chromium and cobalt have been noted in muscle surrounding the implant. Furthermore, elevated levels of cobalt also have been found in the blood, urine, hair and bone adjacent the implant.

We have found that when orthopaedic surgical implants, formed of Co-Cr-Mo alloys, such as F-75 and/or HS-21 alloys, are treated according to the invention, their ion release under static, stress and crevice corrosion and corrosive wear conditions is materially reduced. One preferred process according to the invention essentially includes the provision of a workpiece, formed as an orthopaedic surgical implant from such a cobalt-based alloy as above described, with a coating of biologically compatible elements such as a noble metal, followed by exposing the thus coated surface thereof to bombardment by an ion beam. During the ion beam bombardment, a plurality of the noble metal atoms, together with a plurality of ions from the ion beam, are driven into the surface of the workpiece to a certain preferred depth and are there thoroughly intermixed with, and become interspersed throughout, the atoms of the cobalt-based metal alloy. Preferably, during the ion beam bombardment, the noble metal coating is removed, as by sputtering, from the surface of the workpiece. Of course, workpieces made of cobalt-based alloys and treated according to the invention can find uses other than and in addition to as orthopaedic surgical implants, where corrosion resistance is of import, and such other uses will readily suggest themselves to those skilled in the art. In another preferred process according to the invention, the coating of the workpiece is omitted and, instead, the biologically compatible elements are driven into the surface of the workpiece directly by and from the ion beam when the workpiece is exposed thereto. This is somewhat simpler since there is now no need to remove any coating from the surface of the treated workpiece.

It is known that the rate of corrosion of metal is a function of the electrochemical properties of the metal surface and the chemical composition of the electrolyte to which the metal is exposed over time. We now expect surgical prostheses to remain implanted and useful for about twenty years or more. A service life of such long duration may well render critical the pathological effects of the metallic ion release products on the body of the recipient.

In the metal alloy workpiece treated according to the invention, the surface of the Co-Cr-Mo metal alloy is modified to a predetermined depth, modifying thereby the corrosion effects at the treated surface. The corrosion effects are modified, among others, by shifting the corrosion potential of the metal alloy from an active range to a passive range and, by passivating the electrochemically active sites on the metal surface by injecting into and interspersing atoms of biologically compatible elements with the atoms of the metal alloy to a depth sufficient to inhibit the release of metal ions even under prolonged exposure to the corrosive elements of the human body environment.

Our preferred process of the invention in effecting such surface treatment of a metal alloy is illustrated in FIGS. 1-4. There, a fragmentary portion 10 of a Co-Cr-Mo metal alloy is shown, on an enlarged scale, with its constituent plurality of atoms 12 illustrated as dots. Although the fragmentary portion 10 of the Co-Cr-Mo metal alloy can form a part of any workpiece needed in applications where high corrosion resistance is a required property, preferably the illustrated fragmentary portion 10 is that of an orthopaedic surgical implant, such as a knee or hip joint illustrated in said copending U.S. application Ser. No. 861,845, titled "Ion Implantation of Titanium Workpieces Without Surface Discoloration," the disclosure of which is incorporated herein by reference. Also preferably, the illustrated fragmentary portion 10 is formed of an ASTM F-75 metal alloy, as above specified in its two preferred compositions.

The first step of a process according to the invention to treat the metal alloy, of which the fragmentary portion 10 is a part, so as to impart thereto the desired high degree of corrosion resistance, is to form a coating 16 of a biologically compatible element on a surface 14 of the fragmentary portion 10. The biologically compatible element preferably is a noble metal, such as platinum, gold, palladium and the like. The atoms of the deposited coating 16 of the biologically compatible element are illustrated herein as large black spots 18. The illustration of the atoms 12 of the fragmentary portion 10 of the Co-Cr-Mo metal alloy and of the atoms 18 of the biologically compatible element 16 are for the purpose of better explaining their behavior during the process of the invention and their contribution to the desired result, i.e., to the electrochemical modification of the surface layer of the metal alloy. Preferably, the coating 16 is formed by physical vapor deposition. The coating 16 can equally be effected by other well known processes, such as chemical vapor deposition or electrochemical deposition, however.

The workpiece, whose surface 14, has thus been coated 16 with the biocompatible element, is now ready to be exposed to the bombardment of an ion beam, as that step is illustrated in FIG. 2. This ion beam bombardment of the workpiece can be carried out in any suitable ion implanter, such as a Varian-Extrion 200 kv implanter, an Eaton-Nova implanter, or the implanter illustrated in said copending U.S. application Ser. No. 861,845. The ions in FIG. 2 are indicated by small circles 20, with a positive sign in each of the circles. These ions 20 are energetic ions of a powerful ion beam 22 sufficient to drive a plurality of the atoms 18 of the deposited biologically compatible element forming the coating 16 a predetermined distance into and below the surface 14 of the Co-Cr-Mo metal alloy. This predetermined distance ranges from at least about 0.2 to about 500 nanometers below the surface 14. The energetic ions 20 comprising the powerful ion beam 22 include one or more of the following group: ionized argon, neon, helium, krypton, nitrogen, tantalum and the like. The energetic ions 20 not only drive some of the atoms 18 of the deposited biologically compatible element into and below the surface 14 of the metal alloy, but in addition, some of these ions 20 proceed through the deposited coating 16 and hence become embedded throughout the atoms 12 of the metal alloy. These implanted ions 20, together with the atoms 18 of the biocompatible element driven into the metal alloy, form a mixed zone 24 therein. In this mixed zone 24, the respective atoms 12 of the original metal alloy 10 and the atoms 18 of the biocompatible element become not only interspersed with one another but also with the energetic ions 20 implanted into the metal alloy. It is believed that the atoms 18 of the biocompatible element are driven into the surface 14 of the metal alloy by cascade collisions or by radiation-induced diffusion by the energetic ions 20.

The step involving the bombardment of the coated surface 14 of the metal alloy with the energetic ions 20 of the ion beam 22 is effected over a time period from about one-half hour to about three hours. The ions 20 in the ion beam 22 preferably have an incident energy in the range of about 10 keV to about 500 keV, and preferably between about 120 keV and about 170 keV, and a surface fluence at the surface 14 in the range from about $1 \times 10^{16}$ cm$^{-2}$ to about $5 \times 10^{17}$ cm$^{-2}$.

The ion beam bombardment just described, also acts to remove the coating 16 of the biocompatible element from the surface 14 of the Co-Cr-Mo metal alloy, as indicated by the arrows 26 in FIG. 3, signifying the sputtering. The result is a high corrosion resistant Co-Cr-Mo metal alloy 30, FIG. 4, with a surface layer 32 which includes atoms 18 of the biocompatible element as well as energetic ions 20 of the ion beam 22 intermixed with and dispersed throughout the atoms 12 of the metal alloy 30. The thickness of the coating 16 is chosen so that no coating 16 remains once the ion beam bombardment accomplishes its above-described twofold task.

A second preferred process of the invention omits the forming of the coating 16 of biologically compatible elements on the surface 14 of the metal alloy 10. Instead, this second process proceeds immediately to the ion implantation of the surface 14 of the metal alloy so as to create a mixed zone in the surface layer thereof including a plurality of energetic ions implanted into this mixed zone, with the ions thoroughly intermixed with and dispersed throughout the atoms 12 of the metal alloy. In the second process, the thickness of the surface layer with the mixed zone ranges from about 20 to about 200 nanometers. The energies of the implanted ions, with the ion of choice being singly ionized nitrogen, range from about 50 to about 100 keV, having a surface fluence from about $1 \times 10^{17}$ cm$^{-2}$ to about $5 \times 10^{17}$ cm$^{-2}$. When the ion of choice is, for example, tantalum, the energies of the implanted ions are somewhat higher, namely in the range of about 100 kev to about 500 kev and a surface fluence of about $1 \times 10^{15}$ cm$^{-2}$ to about $2 \times 10^{17}$ cm$^{-2}$. With no coating 16 having been applied to the surface 14, there is now no need to proceed to remove it either. This second process is thus simpler and less expensive than is the first preferred process above described. The second process, however, does not introduce any atoms 18 of a coating 16, such as platinum or gold or palladium, into the surface layer of the metal alloy, as does the first preferred process. Its resultant surface characteristics are, consequently, also different.

Figure 6:
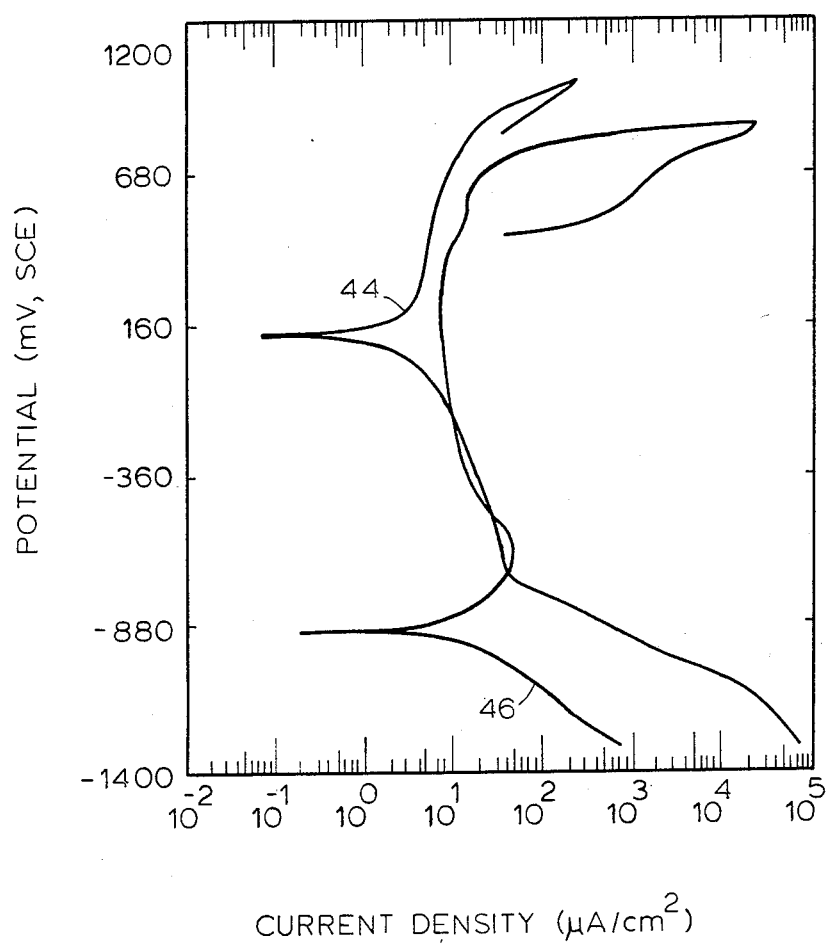
FIG. 6 is a view similar to that shown in FIG. 5, but illustrates the electrochemical response of a Co-Cr-Mo metal alloy which has been treated according to the invention but exposed to a different ion beam than in FIG. 2 versus a Co-Cr-Mo metal alloy which has not been so treated.

In FIGS. 5 and 6, the electrochemical responses of Co-Cr-Mo metal alloys treated according to the processes of the invention are illustrated and compared to Co-Cr-Mo metal alloys which were not so treated.

Specifically, in FIG. 5, curve 36 plots the current density against the voltage with respect to a Standard Calomel Electrode (S.C.E.) at the surface 14 of a treated Co-Cr-Mo metal alloy, while curve 38 plots the same measurements of a not so teated Co-Cr-Mo metal alloy. These potentiodynamic voltage-current density plots have been obtained in an isotonic Ringer's solution. The treated Co-Cr-Mo metal alloy has been surface treated according to the second preferred process just described. Specifically, the metal alloy has been exposed to ion bombardment by singly ionized nitrogen ($N^+$) in an ion implanter as above described, with the following implant specifications: ion energy level 70 keV; surface fluence $3 \times 10^{17}$ cm$^{-2}$; depth of ion implantation below the surface 100 nm; and length of exposure to the ion beam, one hour.

Observation of the curve 36 in relation to the curve 38 of the untreated metal alloy reveals that the electrochemical current density of the treated sample has been considerably reduced versus the untreated control sample at most potentials and especially at those potentials where metallic ion release heretofore had been most troublesome. The reduction in the electrochemical current density of the treated sample metal alloy has now been accompanied by considerable reduction in the metallic ion release therefrom, whether tested under static, stress or crevice corrosion or corrosive wear conditions. We have found that this modification in the electrochemical corrosion potential of the Co-Cr-Mo metal alloy pushed the alloy into a range of potential in which self-passivation of the treated surface 14 occurs spontaneously, even after removal of parts or all of the passive surface layer from the surface 14 of the metal alloy occurs, whether such removal is effected by mechanical abrasion, electrical or chemical means.

In FIG. 6 on the other hand, curve 44 plots the current density against the voltage at the surface 14 of a Co-Cr-Mo metal alloy, which has been treated according to the first preferred method described above, while curve 46 plots the same measurements of a not-so-treated control sample Co-Cr-Mo metal alloy. The treated metal alloy sample thus has, in addition to the ions 20 implanted below its surface 14, also a plurality of atoms 18 of platinum (Pt) imbedded therein and thoroughly mixed with the atoms of the metal alloy, as above described.

Specifically, this Co-Cr-Mo metal alloy sample has been treated as follows. Its surface 14 has been given a thick coating 16 of platinum, with a thickness of 65 nm, by physical vapor deposition. Thereafter, the thus coated surface of the sample has been exposed to ion bombardment in an ion implanter, as above described, to an energetic beam 22 of inert gas ions 20, namely argon, at an energy level of about 160 keV, with a surface fluence of $3 \times 10^{16}$ cm$^{-2}$, to a depth of ion implantation below the surface 14 of 50 nm, after having been exposed to the ion beam 22 for a time period of about 1.5 hours. Following the ion implantation step, no platinum coating remained on the metal alloy surface 14.

Observation of the curve 44 in relation to the curve 46 of the untreated metal alloy reveals that the open circuit corrosion potential of the treated sample has increased considerably over the untreated control sample, i.e., by more than one volt and thus has been shifted to a range where self-passivation of the surface 14 occurs spontaneously, even after partial or complete removal of the original surface layer by mechanical, electrical or chemical means. As a consequence, metallic ion release through this treated surface 14 of the metal alloy has been continually reduced due to the surface modification whether tested under static, stress or crevice corrosion and corrosive wear conditions. The result is a Co-Cr-Mo metal alloy whose corrosion resistance, when exposed to corrosive electrolytes, especially those found in the human body, has been markedly improved.

Thus it has been shown and described a Co-Cr-Mo metal alloy with a markedly improved passive surface layer, hence displaying an increased level of corrosion resistance so as to better serve as a human surgical implant, and a process of effecting such treated surface therein, which product and process satisfy its objects and advantages set forth above.

Since certain changes may be made in the present disclosure without departing from the scope of the present invention, it is intended that all matter described in the accompanying drawings, be interpreted in an illustrative and not in a limiting sense.

What is claimed is:

1. A process of passivating the electrochemically active surface of a metal alloy comprising:
   (a) providing a workpiece formed of said metal alloy, said metal alloy being a combination of chromium, nickel, iron, carbon, cobalt, and either molybdenum or manganese and silicon in lieu of molybdenum;
   (b) forming a coating of a biocompatible element on the surface of said workpiece, said coating being formed by physical vapor deposition and to a thickness in the range from about 20 nm to about 200 nm, and said biocompatible element being one of a group consisting of platinum, gold and palladium;
   (c) exposing said coated surface of said workpiece to an ion beam so as to drive a plurality of atoms of said biocompatible element from said coating, together with a plurality of ions from said ion beam, into said surface of said workpiece at a distance ranging from about 0.2 to about 200 nanometers, said ion beam including ions from one of a group consisting of ionized nitrogen, tantalum, argon, neon, helium and krypton; and
   (d) removing the remainder of said coating from said surface of said workpiece.

2. The process of claim 1 wherein said removing said remainder of said coating is effected by said ion beam, and wherein said ion beam has a preferred incident energy on said coated surface in the range from about 100 keV to about 500 keV and a surface fluence in the range from about $1 \times 10^{15}$ cm$^{-2}$ to about $5 \times 10^{17}$ cm$^{-2}$.

3. The process of claim 1 wherein said passivated metal alloy has acquired spontaneous self-passivation even after removal of said surface of said workpiece containing said plurality of biocompatible metal element atoms and said plurality of ions at said distance from about 0.2 to about 500 nanometers.

* * * * *

UNITED STATES PATENT AND TRADEMARK OFFICE
CERTIFICATE OF CORRECTION

PATENT NO. : 4,743,308

DATED : May 10, 1988

INVENTOR(S) : Piran Sioshansi and Ward D. Halverson

It is certified that error appears in the above-identified patent and that said Letters Patent is hereby corrected as shown below:

Please insert in colum 1, line 3, right after the title, the following clause:

--This invention was made with Government support under grant "1R43AM36792-01" awarded by the National Institutes of Health. The government has certain rights in the invention. --

Signed and Sealed this

Twelfth Day of October, 1993

Attest:

BRUCE LEHMAN

Attesting Officer

Commissioner of Patents and Trademarks